US006395778B1

(12) United States Patent
Luthria

(10) Patent No.: US 6,395,778 B1
(45) Date of Patent: May 28, 2002

(54) PROCESS FOR MAKING AN ENRICHED MIXTURE OF POLYUNSATURATED FATTY ACID ESTERS

(75) Inventor: Devanand L. Luthria, Ankeny, IA (US)

(73) Assignee: OmegaTech, Inc., Boulder, CO (US)

( * ) Notice: Subject to any disclaimer, the term of this patent is extended or adjusted under 35 U.S.C. 154(b) by 0 days.

(21) Appl. No.: 09/758,973

(22) Filed: Jan. 11, 2001

Related U.S. Application Data

(60) Provisional application No. 60/175,583, filed on Jan. 11, 2000.

(51) Int. Cl.[7] ........................................ A61K 31/22
(52) U.S. Cl. ........................................ 514/549
(58) Field of Search ........................................ 514/549

(56) References Cited

U.S. PATENT DOCUMENTS

| | | | | |
|---|---|---|---|---|
| 2,870,061 | A | 1/1959 | Huggins | 167/56 |
| 2,871,158 | A | 1/1959 | Cardaciotto et al. | 167/56 |
| 2,885,322 | A | 5/1959 | Klotz | 167/56 |
| 2,903,397 | A | 9/1959 | Heilig et al. | 167/82 |
| 3,035,973 | A | 5/1962 | Klotz | 167/56 |
| 3,080,286 | A | 3/1963 | Neary | 167/56 |
| 3,155,577 | A | 11/1964 | Mercer et al. | 167/56 |
| 4,070,456 | A | 1/1978 | Kazan et al. | 424/173 |
| 4,145,446 | A | 3/1979 | Kurucz et al. | |
| 4,271,142 | A | 6/1981 | Puglia et al. | 424/14 |
| 4,377,526 | A | 3/1983 | Fujita et al. | |
| 4,605,551 | A | 8/1986 | Buehler et al. | 424/38 |
| 4,615,839 | A | 10/1986 | Seto et al. | |
| 4,623,488 | A | 11/1986 | Takao | |
| 4,670,285 | A | 6/1987 | Clandinin et al. | |
| 4,776,984 | A | 10/1988 | Traitler et al. | |
| 4,792,418 | A | 12/1988 | Rubin et al. | |
| 4,843,095 | A | 6/1989 | Rubin | |
| 4,874,629 | A | 10/1989 | Chang et al. | |
| 5,006,281 | A | 4/1991 | Rubin et al. | |
| 5,023,100 | A | 6/1991 | Chang et al. | |
| 5,034,415 | A | 7/1991 | Rubin | |
| 5,106,542 | A | 4/1992 | Traitler et al. | |
| 5,130,242 | A | 7/1992 | Barclay | |
| 5,130,449 | A | 7/1992 | Lagarde et al. | |
| 5,133,963 | A | 7/1992 | Ise | |
| 5,215,630 | A | 6/1993 | Hata et al. | |
| 5,243,046 | A | 9/1993 | Traitler et al. | |
| 5,340,594 | A | 8/1994 | Barclay | |
| 5,340,742 | A | 8/1994 | Barclay | |
| 5,480,787 | A | 1/1996 | Negishi et al. | |
| 5,502,077 | A | 3/1996 | Breivik et al. | |
| 5,516,524 | A | 5/1996 | Kais et al. | 424/439 |
| 5,518,918 | A | 5/1996 | Barclay | |
| 5,539,133 | A | 7/1996 | Kohn et al. | |
| 5,547,699 | A | 8/1996 | Iisuka et al. | |
| 5,656,319 | A | 8/1997 | Barclay | |
| 5,688,500 | A | 11/1997 | Barclay | |
| 5,693,358 | A | 12/1997 | Park et al. | |
| 5,698,244 | A | 12/1997 | Barclay | |
| 5,883,273 | A | 3/1999 | Miller et al. | |
| 5,908,622 | A | 6/1999 | Barclay | |
| 5,935,828 | A | 8/1999 | Zaks et al. | |
| 5,945,318 | A | 8/1999 | Breivik et al. | |

FOREIGN PATENT DOCUMENTS

| | | |
|---|---|---|
| EP | 0 255 824 B1 | 1/1990 |
| EP | 0 969 086 A1 | 1/2000 |

OTHER PUBLICATIONS

Connie M. Weaver, Ph.D., Meeting Optimal Calcium Requirements, The Journal of the American Medical Association, pp. 69–71, 1994.

Optimal Calcium Intake–NIH Consensus Conference, The Journal of the American Medical Association, pp. 1942–1948, 1994.

Official Monographs/Docusate, The U.S. Pharmacopoeia & Nat. Formulary, pp. 597–601, 2000.

Product Information, British Pharmacopoeia, pp. 960–961, 1999.

Gastro–intestinal Agents, Martindale, The Extra Pharmacopoeia, 31st Edition, The Royal Pharmaceutical Society, pp. 1216–1217(1985).

Docusate Preparations, British Pharmacopoeia, pp. 1797–1800, 1999.

Official Monographs/Senna, The U.S. Pharmacopoeia & Nat. Formulary, pp. 1516–1517, 2000.

Abu–Nasr et al., Highly Unsaturated Fatty Acids. II. Fractionation by Urea Inclusion Compounds, *J. Amer. Oil Chemists' Society*, Jan. 1954, pp. 16–20, vol. 31.

(List continued on next page.)

*Primary Examiner*—Raymond Henley, III
(74) *Attorney, Agent, or Firm*—Sheridan Ross P.C.

(57) ABSTRACT

This invention is directed to a process for making an enriched mixture comprising a polyunsaturated fatty acid ester having the Formula (V):

(V)

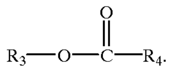

In one embodiment, this process comprises transesterifying an oil from Schizochytrium sp. with an alcohol in the presence of a base to form a saturated fatty acid ester and the polyunsaturated fatty acid ester (the fatty acid esters are formed from the alcohol and fatty acid residues of at least one glyceride in the oil). Urea is subsequently dissolved in a medium comprising the fatty acid esters to form a medium comprising the fatty acid esters and dissolved urea. This medium is then cooled or concentrated to form (a) a precipitate comprising urea and at least a portion of the saturated fatty acid ester, and (b) a liquid fraction comprising at least most of the polyunsaturated fatty acid ester. Afterward, the precipitate and liquid fraction are separated. In this embodiment, the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

64 Claims, No Drawings

OTHER PUBLICATIONS

Swern, D., "Techniques of Separation, E. Urea Complexes," Chapter XX, pp. 2309–2358 (No date available).

Schlenk, H., "Urea Inclusion Compounds of Fatty Acids," Canad. J. Research, sect. B 25 (1947), pp. 243–267.

"The Analysis of Fatty Acids," pp. 147–149 (No date available).

Nakahara, T., "Production of Docosahexaenoic and Docosapentaenoic Acids by Schizochytrium sp. Isolated from Yap Islands," JAOCS, vol. 73, No. 11 (1996), pp. 1421–1426.

Teshima, S., "Separation of Polyunsaturated Fatty Acids by Column Chromatography on a Silver Nitrate–Impregnated Silica Gel," Bulletin of the Japanese Society of Scientific Fisheries, vol. 44, No. 8, 1978, p. 927.

Abu–Nasr, A., "Highly Unsaturated Fatty Acids. III. Isolation of Methyl Eicosapentaenoate, Ethyl Docosapentaenoate and Ethyl Docosahexaenoate from Cod Liver Oil Esters by Chromatography," The Journal of the American Oil Chemists' Society, vol. 31, No. 2, Feb. 1954, pp. 41–45.

Abu–Nasr, A., "Highly Unsaturated Fatty Acids. II. Fractionation by Urea Inclusion Compounds," Journal of the American Oil Chemists' Society, Jan. 1954, pp. 16–20.

"Monitoring Detergent Safety Downstream," Journal of the American Oil Chemists' Society, Apr. 1989, vol. 66., No. 4, 4 pages.

PROCESS FOR MAKING AN ENRICHED MIXTURE OF POLYUNSATURATED FATTY ACID ESTERS

This application claims the benefit or provisional U.S. application No. 60/175,583 filed Jan. 11, 2000.

FIELD OF THE INVENTION

This invention relates generally to a process for making an enriched mixture of esters of polyunsaturated fatty acids from a natural source containing a high concentration of glycerides (particularly triglycerides) which comprise one or more polyunsaturated fatty acid residues. In a particularly preferred embodiment, this invention is directed to making an enriched mixture of esters of polyunsaturated fatty acids (particularly esters of docosahexaenoic acid) from an oil obtained from the marine algae identified as Schizochytrium sp.

BACKGROUND OF THE INVENTION

Many polyunsaturated fatty acids are known to have therapeutic and nutritional benefits. One such fatty acid is docosahexaenoic acid ("DHA"). DHA is a 22-carbon, naturally occurring, unbranched fatty acid comprising 6 carbon-carbon double bonds (with the biologically active form containing all cis carbon-carbon double bonds). DHA and many of its derivatives (e.g., esters comprising a DHA residue, particularly the ethyl ester of DHA and triglycerides containing one or more DHA residues) have been used, for example, to treat cardiovascular and inflammatory diseases. They also have been added to infant milk to promote the development of brain and retina functions. Use of DHA esters (as opposed to the free DHA fatty acid) is often particularly advantageous because such esters (especially the ethyl ester and triglycerides) tend to have a palatable taste and tend to be easily absorbed by animal digestive systems.

Sources of DHA and derivatives thereof include marine animal oils, fish oils (e.g., menhaden oil, salmon oil, mackerel oil, cod oil, herring oil, sardine oil, capelin oil, and tuna oil), marine algae (e.g., Schizochytrium sp.), and human milk. Such sources, however, normally contain a substantial amount of saturated fatty acid residues (often as residues of triglyceride molecules) which dilute the concentration of DHA residues in the oil. It is therefore advantageous to reduce the concentration of undesirable saturated fatty acid residues in the oil while increasing the concentration of DHA or a derivative(s) thereof.

Numerous methods have been used alone or in combination to isolate (or at least concentrate) and recover specific fatty acids and their derivatives from various naturally occurring sources. These processes include fractional crystallization at low temperatures, molecular distillation, urea adduct crystallization, extraction with metal salt solutions, super critical fluid fractionation on countercurrent columns, and high performance liquid chromatography.

In W. W. Christie, *Lipid Analysis*, pp. 147–49 (Pergamon Press, 1976), a method is disclosed generally for using urea to separate methyl esters of saturated fatty acids from a mixture which also contains methyl esters of polyunsaturated fatty acids. According to Christie, when urea is permitted to crystallize in the presence of various long-chain aliphatic compounds, it forms hexagonal crystals which incorporate the aliphatic compounds (a urea crystal which incorporates an aliphatic compound is sometimes referred to as a "urea complex"), thereby allowing the aliphatic compounds to be easily separated from the solution via filtration. Christie states generally that methyl esters of saturated fatty acids form urea complexes more readily than methyl esters of unsaturated fatty acids having the same length, and that methyl esters of unsaturated fatty acids having trans double bonds form urea complexes more readily than methyl esters of analogous fatty acids having cis double bonds. Christie also reports using urea crystallization to concentrate methyl esters of polyunsaturated fatty acids from a mixture containing methyl esters of polyunsaturated fatty acids and methyl esters of saturated fatty acids.

Another reference directed to separating methyl esters of fatty acids using urea crystallization is T. Nakahara, T. Yokochi, T. Higashihara, S. Tanaka, T. Yaguchi, & D. Honda, "Production of Docosahexaenoic and Docosapentaenoic Acids by Schizochytrium sp. Isolated from Yap Islands," *JAOCS*, vol. 73, no. 11, pp. 1421–26 (1996). Nakahara et al. report making a mixture of methyl esters of fatty acids by washing and drying Schizochytrium sp. cells, and then methyl-esterifying the cells directly with methanol in the presence of 10% HCl. Nakahara et al. report that 34.9% of the resulting methyl esters contained DHA residues, and 8.7% contained DPA residues. To concentrate these polyunsaturated fatty acid methyl esters, Nakahara et al. report adding methanol and urea to the mixture, heating the mixture to 60° C. to dissolve the urea, and then cooling the mixture to 10° C. to crystallize the urea. Nakahara et al. report that they were able to recover 73.3% of the DHA methyl esters and 17.7% of the DPA methyl esters using this method.

The growing use of polyunsaturated fatty acids (particularly DHA) and esters thereof in medical and nutritional applications has created a further need for a cost-effective and reliable process that may be used to prepare a composition comprising an enriched concentration of polyunsaturated fatty acid compounds (and a minimal concentration of saturated fatty acid compounds) from sources (particularly naturally occurring sources) of glycerides having at least one polyunsaturated fatty acid residue.

SUMMARY OF THE INVENTION

This invention provides for a novel and useful process for making an enriched composition comprising polyunsaturated fatty acid compounds (particularly compounds containing a DHA residue). This process is particularly advantageous because it provides a method for enrichment of polyunsaturated fatty acid esters (e.g., methyl and ethyl esters) despite the fact that: (1) the compounds involved here are highly complex molecules (e.g., they contain carbon chains having from 3 to 21 carbon atoms and up to 6 double bonds), and (2) there often is only a subtle difference in structure between polyunsaturated fatty acid compounds and many saturated fatty acid compounds.

Briefly, therefore, this invention is directed to a process for making a mixture comprising a polyunsaturated fatty acid ester having the Formula (V):

(V)

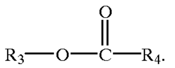

In one embodiment, the process comprises transesterifying an oil from Schizochytrium sp. with an alcohol in the presence of a base to form a saturated fatty acid ester and the polyunsaturated fatty acid ester (these fatty acid esters are formed from the alcohol and fatty acid residues of at least one glyceride in the oil). Urea is subsequently dissolved in a medium comprising the fatty acid esters to form a medium comprising the fatty acid esters and dissolved urea. This medium is then cooled or concentrated to form (a) a precipitate comprising urea crystals and at least a portion of the saturated fatty acid ester, which is trapped within the urea crystals; and (b) a liquid fraction comprising at least most of the polyunsaturated fatty acid ester. Afterward, the precipitate is separated from the liquid fraction. Here, the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

In another embodiment, the process comprises transesterifying an oil from Schizochytrium sp. with an alcohol in the presence of an acid to form a saturated fatty acid ester and the polyunsaturated fatty acid ester (these fatty acid esters are formed from the alcohol and fatty acid residues of at least one glyceride in the oil). Urea is subsequently dissolved in a medium comprising the fatty acid esters to form a medium comprising the fatty acid esters and dissolved urea. This medium, in turn, is cooled to a temperature of no less than about 15° C. to form (a) a precipitate comprising urea crystals and at least a portion of the saturated fatty acid ester, which is trapped within the urea crystals; and (b) a liquid fraction comprising at least most of the polyunsaturated fatty acid ester. Afterward, the precipitate is separated from the liquid fraction. Here, the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

In another embodiment, the process comprises transesterifying an oil from Schizochytrium sp. with an alcohol in the presence of an acid to form a reaction mixture comprising a saturated fatty acid ester and the polyunsaturated fatty acid ester (the fatty acid esters are formed from the alcohol and fatty acid residues of at least one glyceride in the oil). At least most of the polyunsaturated fatty acid ester is subsequently separated from the reaction mixture to form a mixture comprising the polyunsaturated fatty acid and a residual amount of the saturated fatty acid ester. Urea is then dissolved in a medium comprising the separated polyunsaturated fatty acid ester and residual saturated fatty acid ester to form a medium comprising the separated polyunsaturated fatty acid ester, residual saturated fatty acid ester, and dissolved urea. This medium, in turn, is cooled or concentrated to form (a) a precipitate comprising urea crystals and at least a portion of the residual saturated fatty acid ester, which is trapped within the urea crystals; and (b) a liquid fraction comprising at least most of the separated polyunsaturated fatty acid ester. Afterward, the precipitate is separated from the liquid fraction. Here, the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

In another embodiment, the process comprises transesterifying an oil from Schizochytrium sp. with an alcohol in the presence of an acid to form a saturated fatty acid ester and the polyunsaturated fatty acid ester (these fatty acid esters are formed from the alcohol and fatty acid residues of at least one glyceride in the oil). Urea is subsequently dissolved in a medium comprising the fatty acid esters to form a medium comprising the fatty acid esters and dissolved urea. This medium, in turn, is cooled to a temperature of no less than 10° C. to form (a) a precipitate comprising urea crystals and at least a portion of the saturated fatty acid ester, which is trapped within the urea crystals; and (b) a liquid fraction comprising at least most of the polyunsaturated fatty acid ester. Afterward, the precipitate is separated from the liquid fraction. Here, the alcohol is $R_3$—OH, $R_3$ comprises at least 2 carbon atoms and is a hydrocarbyl or substituted hydrocarbyl, and $R_4$ is a straight chain hydrocarbyl comprising 21 carbon atoms and at least 2 carbon-carbon double bonds.

In another embodiment, the process comprises forming the polyunsaturated fatty acid ester and a saturated fatty acid ester (these fatty acid esters are formed from at least one glyceride obtained from Schizochytrium sp.). A solvent comprising the fatty acid esters is subsequently cooled to a temperature of no less than about −30° C. and no greater than about 0° C. to form (a) a precipitate comprising at least a portion of the saturated fatty acid ester, and (b) a liquid fraction comprising at least most of the polyunsaturated fatty acid ester. Afterward, the precipitate is separated from the liquid fraction. Here, the saturated fatty acid ester has Formula (VI):

(VI)

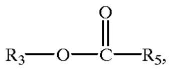

$R_3$ is a hydrocarbyl or a substituted hydrocarbyl, $R_4$ is a straight chain hydrocarbyl comprising 21 carbon atoms and at least 2 carbon-carbon double bonds, and $R_5$ is a hydrocarbyl comprising no double bonds.

Other features of this invention will be in part apparent and in part pointed out hereinafter.

DETAILED DESCRIPTION OF THE PREFERRED EMBODIMENT

In accordance with the present invention, a novel and useful process has been developed for making a composition containing an enriched concentration of polyunsaturated fatty acid esters (particularly esters containing a DHA residue) from sources which comprise a glyceride having at least one polyunsaturated fatty acid residue. This process generally comprises 2 steps: (1) transesterifying the starting material to form a polyunsaturated fatty acid ester (particularly an ester of DHA) and a saturated fatty acid ester; and (2) separating the polyunsaturated fatty acid ester from at least a portion of the saturated fatty acid ester via urea crystallization or winterization, thereby enriching the concentration of the polyunsaturated fatty acid ester.

A. Starting Material

The starting materials that may be used in accordance with this invention vary widely. Preferably, the starting material is a naturally occurring source that comprises at least one glyceride (most preferably a triglyceride) which comprises at least one polyunsaturated fatty acid residue. In a particularly preferred embodiment, at least about 10% (more preferably at least about 25%, and most preferably at least about 30%) of the fatty acid residues in the source are the desired polyunsaturated fatty acid residues. Where, for example, the desired polyunsaturated fatty acid compound is DHA or a derivative thereof, the source preferably is a marine animal oil, fish oil (e.g., menhaden oil, salmon oil, mackerel oil, cod oil, herring oil, sardine oil, capelin oil, and tuna oil), marine algae, or human milk. In an especially preferred embodiment, the DHA source is the oil from the marine algae identified as Schizochytrium sp. This oil is commercially available, for example, under the trade name SEAGOLD from Monsanto Co. (St. Louis, Mo.).

(I)

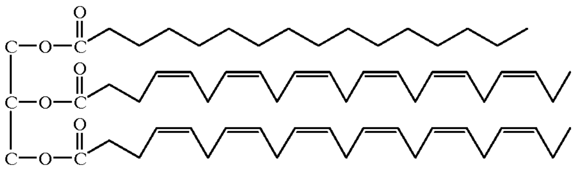

To illustrate further, a triglyceride having a 4,7,10,13,16,19–22:6 residue; a 4,7,10,13,16–22:5 residue (i.e., a DPA fatty acid residue containing 22 carbon atoms and 5 carbon-carbon cis double bonds between the 4th & 5th, 7th & 8th, 10th & 11th, 13th & 14th, and 16th & 17th carbon atoms, counting from the carbonyl group of the residue, the carbon of the carbonyl group being the first carbon counted); and a palmitic acid residue may have the following Formula (II):

(II)

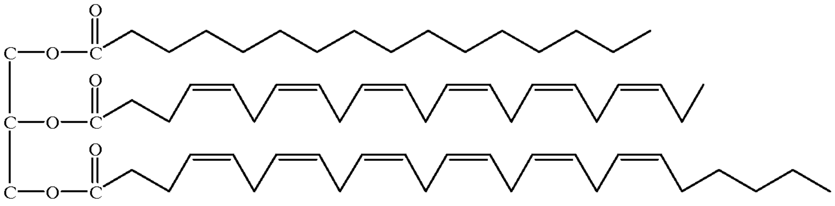

As used herein, a "glyceride" is an ester of glycerol and at least one fatty acid, wherein from 1 to 3 of the hydroxyl groups of the glycerol have been replaced by a fatty acid residue. Where multiple fatty acid residues are present, the fatty acid residues may be the same or different.

In many suitable starting materials, the bulk of glycerides are triglycerides. A "triglyceride" is an ester of three fatty acid residues and glycerol, and has the general chemical formula: $CH_2(OOCR^1)CH(OOCR^2)CH_2(OOCR^3)$, wherein $OOCR^1$, $OOCR^2$, and $OOCR^3$ are each fatty acid residues. To illustrate, a triglyceride having two 4,7,10,13,16,19–22:6 residues (i.e., a DHA fatty acid residue containing 22 carbon atoms and 6 carbon-carbon cis double bonds between the 4th & 5th, 7th & 8th, 10th & 11th, 13th & 14th, 16th & 17th, and 19th & 20th carbon atoms, counting from the carbonyl group of the residue, the carbon of the carbonyl group being the first carbon counted) and one palmitic acid residue (ie., a fatty acid residue comprising 16 carbon atoms containing no carbon-carbon double bonds) may have the following Formula As shown in Formulas (I) and (II), each fatty acid residue may be either saturated (i.e., all the bonds between the carbon atoms are single bonds ) or unsaturated (i.e.,there is at least one carbon-carbon double or triple bound). Unsaturated fatty acid residues are sometimes identified herein by an omega ("ω") number. This number denominates the position of the first double bond, when counting from the terminal methyl group of the fatty acid or fatty acid residue. For example, in Formulas (I) and (II), the DHA residue are ω-3 fatty acid residues. The DPA residue in Formula (II), on the other hand, is an ω-6 fatty acid residue. Generally, polyunsaturated fatty acid residue having the most beneficial medical and nutritional properties are ω-3 fatty acid residues.

B. Transesterification of the Glycerides in the Starting Material to Form Separate Esters of the Fatty Acid Residues of the Glycerides The purpose of the transesterification step is to cleave the fatty acid residues from the glycerol backbone of the glycerides in the starting material and form separate esters of each of the residues so that they can be isolated from each other. As used rein, an ester of a fatty acid residue has the following Formula (III):

(III)

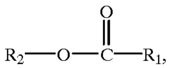

wherein $R_1$ is the straight hydrocarbyl chain of the fatty acid residue, and $R_2$ is a hydrocarbyl or substituted hydrocarbyl. For example, the methyl ester of 4,7,10,13,16,19–22:6 having all cis carbon-carbon double bonds (i.e., the methyl ester of DHA) has the following Formula (IV):

(IV)

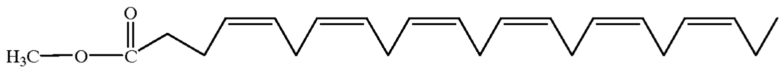

In a preferred embodiment, the glycerides are transesterified to form alkyl esters of the fatty acid residues. These alkyl esters preferably are lower alkyl esters (i.e., $R_2$ in Formula (III) is a hydrocarbyl containing from 1 to 6 carbon atoms). More preferably, the esters are methyl esters or ethyl esters (i.e., $R_2$ in Formula (III) is a hydrocarbyl containing 1 or 2 carbon atoms). Most preferably, the esters are ethyl esters (i.e., $R_2$ in Formula (III) is a hydrocarbyl containing 2 carbon atoms). Ethyl esters typically taste better and are less toxic (e.g., when ethyl esters hydrolyze in the digestive tract to form free fatty acids, they produce ethanol as a byproduct; on the other hand, the hydrolysis of methyl esters produces methanol as a byproduct, which is generally more toxic than ethanol).

In a particularly preferred embodiment of this invention, the transesterification reaction is catalyzed by a base or an acid. This reaction comprises contacting the starting material with an alcohol in the presence of the base or acid, as the following reaction illustrates for a triglyceride starting material:

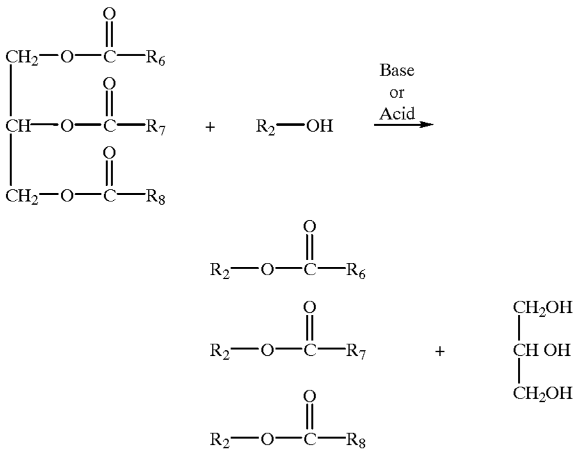

wherein $R_2$—OH is the alcohol; $R_2$ is a hydrocarbyl or a substituted hydrocarbyl; and $R_6$, $R_7$, and $R_8$ are the straight hydrocarbyl chains of the fatty acid residues. It is presently believed that, during base-catalyzed transesterification, the alcohol is de-protonated to form an oxide ion, which, in turn, attacks the carbonyl groups on the triglyceride to form separate $R_2$-esters of each of the fatty acid residues of the triglyceride. During acid-catalyzed transesterification, on the other hand, the carbonyl oxygen atoms of the glyceride are protonated and then subjected to nucleophilic attack by the alcohol to form the separate $R_2$-esters of each of the fatty acid residues.

Because formation of lower alkyl esters is generally preferred, the alcohol preferably is a lower alkyl alcohol containing from 1 to 6 carbon atoms. More preferably, the alcohol is methanol (which reacts with glycerides to form methyl esters of the fatty acid residues) or ethanol (which reacts with glycerides to form ethyl esters of the fatty acid residues). Most preferably, the alcohol is ethanol.

Acid-catalyzed transesterification may be carried out, for example, by incubating a triglyceride at from about 0 to about 150° C. in a mixture containing the alcohol and an acid (e.g., HCl), preferably under a non-oxidizing atmosphere and in the absence of water. In one embodiment, the triglyceridelacid/alcohol mixture is refluxed for at least about 2 hours. In another embodiment, the triglyceride/acid/alcohol mixture is maintained at from about 0 to about 50° C. overnight. The alcohol preferably has the formula $R_2$—OH (wherein $R_2$ is defined above for Formula III), and is selected to form the desired fatty acid ester. For example, methanol may be used to form methyl esters, and ethanol may be used to form ethyl esters. Because acid-catalyzed transesterification is typically reversible, the alcohol preferably is present in a large excess so that the reaction proceeds essentially to completion. Preferably, the triglyceride concentration in the alcohol/acid mixture is from about 0.1 to about 15% by weight, and most preferably about 3% by weight. If the acid is HCl, the concentration of HCl in the alcohol/HCl mixture preferably is from about 4 to about 15% by weight, and most preferably about 10% by weight. Such a mixture may be prepared by various methods known in the art, such as bubbling dry gaseous hydrogen chloride into dry ethanol, or adding 1 ml of acetylchloride to each 10 ml of alcohol (to form approximately 10% by weight HCl in alcohol). Although HCl is most preferred, other acids may alternatively be used. One such acid is or $H_2SO_4$, which typically is used at a concentration of from about 0.5 to about 5% by weight in the alcohol. It should be noted, however, that because $H_2SO_4$ is a strong oxidizing agent, it preferably is not used with long reflux times (i.e., greater than about 6 hours), at high concentrations (i.e., greater than about 5% by weight), or at high temperatures (i.e., greater than 150° C.). Another example of a suitable acid is boron trifluoride, which preferably is used at a concentration of from about 1 to about 20% by weight in the alcohol. Boron trifluoride, however, is less preferred than HCl because boron trifluoride has a greater tendency to produce undesirable byproducts.

A triglyceride alternatively may be transesterified by, for example, base-catalyzed transesterification wherein the triglyceride is transesterified by an alcohol in the presence of a basic catalyst. In this instance, the base may be, for example, sodium methoxide, potassium methoxide, elemental sodium, sodium hydroxide, or potassium hydroxide. Preferably, the volumetric ratio of triglyceride to the base/alcohol mixture is at least about 1:1, and most preferably about 1:2. The concentration of the base in the alcohol preferably is from about 0.1 to about 2 M. In one embodiment, the base-catalyzed transesterification reaction is conducted at room temperature (i.e., at a temperature of from about 20 to about 25° C.) for from about 6 to about 20 hours. In another embodiment, the base-catalyzed transesterification reaction is conducted at a temperature greater than room temperature. In this embodiment, the glyceride/alcohol/catalyst solution preferably is heated to a temperature of at least about 40° C., more preferably from about 70 to about 150° C., and most preferably at about 100° C. In a particularly preferred embodiment, the solution is heated using a reflux condenser so that the reaction mixture may be heated to temperatures above the boiling point of one or more components in the mixture without losing the components into the vapor phase (i.e., when the components vaporize, they rise into the reflux condenser which has a cooler temperature, thereby causing the vapor to condense into a liquid and flow back into the liquid mixture).

During the transesterification reaction, the reacting mixture preferably is placed under a non-oxidizing atmosphere, such as an atmosphere consisting essentially of a noble gas, $N_2$, or a combination thereof. Use of such an atmosphere is particularly preferred if the transesterification reaction is conducted over a period of time exceeding about 10 minutes. An atmosphere consisting essentially of $N_2$ is most preferred due to the relatively low cost of $N_2$. Placing the reacting mixture under a non-oxidizing atmosphere is advantageous because oxidizing atmospheres tend to cause the carbon-carbon double bonds of the polyunsaturated fatty acid residues to oxidize to form, for example, aldehydes and epoxides. Such oxidized residues are undesirable, in part, because they tend to make the fatty acid moieties less palatable. An antioxidant (e.g., ascorbyl palmitate or propyl gallate) may also be added to the reacting mixture to prevent auto-oxidation, and is particularly preferred where a non-oxidizing atmosphere is not used.

The transesterification may be conducted in a mixture comprising an organic solvent. This solvent may vary widely, but preferably is capable of solubilizing the glyceride that comprises the polyunsaturated fatty acid residue. Where the starting material comprises more than one glyceride, the organic solvent preferably is capable of solubilizing all the glycerides. Examples of often suitable solvents include dichloromethane, acetonitrile, ethyl acetate, and diethyl ether. Dichloromethane is presently most preferred.

Following the transesterification reaction, the esters preferably are separated from the reaction mixture by adding water. Often, these esters (which are organic) rise to the top of the reaction mixture and may simply be skimmed from the remaining reaction mixture. This is particularly true in large-scale, industrial applications.

Alternatively, liquid-liquid solvent extraction may be used to separate the esters from the remaining reaction mixture. This extraction may vary widely. In one embodiment, for example, the extraction generally begins by adding water to the mixture, and then extracting the esters with a non-polar solvent. The amount of water added to the reaction mixture may vary widely, and most typically is about 1:1. If the transesterification is base-catalyzed, the water preferably comprises sufficient acid to neutralize the mixture, or, even more preferably, to impart a slightly acidic pH to the mixture. The acid used is not critical, and may, for example, be hydrochloric acid, citric acid, or acetic acid, with hydrochloric acid being most preferred. The ratio of total volume of non-polar solvent to the volume of reaction mass (including the water added) also may vary widely, and is most preferably from about 1:3 to about 4:3. In a particularly preferred embodiment, the mixture is extracted with multiple fractions (preferably 3 fractions) of the non-polar organic solvent which are subsequently combined after the individual extractions are completed. Examples of suitable non-polar solvents include petroleum ether, pentane, hexane, cyclohexane, or heptane, with hexane and petroleum ether being the most preferred. The non-polar solvent also may contain a small amount of slightly polar organic solvent as well, such as diethyl ether. Use of such a slightly polar component tends to improve the extraction of fatty acid esters from the aqueous layer because such esters also are slightly polar. If a slightly polar organic component is used, the volumetric concentration of the slightly polar component to the non-polar component preferably is no greater than about 20%, more preferably no greater than about 10%, and most preferably from about 5 to about 10%. The resulting extraction organic solvent layer may be washed to remove, for example, any residual free acid and/or residual water in the layer. Removal of residual free acid preferably is achieved by washing the layer with an aqueous solution containing a weak base, e.g., an aqueous solution containing about 2% by weight of potassium bicarbonate concentration. Removal of residual water may be achieved, for example, by washing the layer with brine (i.e., a saturated salt solution) and/or passing the layer over an anhydrous salt (e.g., sodium sulfate or magnesium sulfate). If the solvent is washed with brine, the volumetric ratio of brine to solvent preferably is about 1:6.

Following the extraction, the fatty acid esters in the non-polar solvent layer may be concentrated. In one embodiment of this invention, the esters are concentrated by evaporating a portion of the non-polar solvent.

C. Separating the Polyunsaturated Fatty Acid Ester(s) from at Least a Portion of at Least One Saturated Fatty Acid Ester Via Urea Crystallization or Winterization Transesterification of a naturally occurring starting material typically produces other fatty acid esters in addition to the desired polyunsaturated fatty acid ester(s). As noted earlier, many such fatty esters (particularly saturated fatty esters) tend to have unknown and/or adverse medical and nutritional properties. It is therefore often advantageous to remove at least a portion of the saturated fatty esters from the transesterification reaction mixture to form an enriched mixture containing the desired polyunsaturated fatty acid(s). This separation preferably is performed using either urea crystallization or winterization.

1. Urea Crystallization

When urea crystallizes in a solution containing polyunsaturated fatty acid esters (e.g., esters of DHA) and saturated fatty acid esters formed by the transesterification of a glyceride source using the techniques discussed above, a precipitate forms which comprises the urea and at least a portion of the saturated fatty acid esters. This precipitate, however, comprises a substantially lesser fraction of the polyunsaturated fatty acid esters than the initial reaction mixture. The bulk of the polyunsaturated fatty acid esters, instead, remain in solution and can therefore be easily separated from the precipitated saturated fatty acid esters.

The urea crystallization separation process comprises first forming a solution comprising fatty acid esters and urea. The amount of urea preferably is proportional to the total amount of saturated fatty acids to be separated from the solution. When separating fatty acid esters from the transesterification reaction mixtures described above, the mass ratio of the mixture of fatty acid esters to urea is typically about 1:2. The solution also preferably comprises an organic solvent which can solubilize urea and the desired polyunsaturated fatty acid ester, and more preferably can solubilize urea and all the fatty acid esters in the mixture. Examples of often suitable solvents include alkyl alcohols having from 1 to 4 carbons, with methanol and ethanol being more preferred, and ethanol being the most preferred. The volumetric ratio of the mixture of fatty acid esters to solvent is preferably about 1:10.

Essentially all the urea preferably is dissolved in the solution. This may generally be achieved by heating the solution. The solution, however, preferably is not heated to a temperature above the boiling point of the organic solvent. Typically, the solution preferably is heated to a temperature of about 60° C.

Once the urea is dissolved in the solution, the mixture preferably is cooled to form a precipitate comprising urea. Preferably, the solution is cooled to a temperature which is greater than 10° C., more preferably to a temperature which is no less than about 15° C., still more preferably to a temperature which is no less than about 20° C., and most preferably to a temperature of from about 20 to about 25° C. Once the solution is cooled, it preferably is allowed to stand for a period of time (typically no greater than about 20 hours) at the cooling temperature with occasional stirring.

In another embodiment of this invention, after the solution comprising fatty acid esters and dissolved urea is formed, a precipitate comprising urea is formed by concentrating the solution. The solution may be concentrated, for example, by evaporating a portion of the solvent in the solution. The amount of solvent removed preferably is sufficient to cause the urea concentration in the solution to exceed the saturation concentration.

During the urea crystallization separation process, the solution preferably is kept in a non-oxidizing atmosphere, such as an atmosphere consisting essentially of a noble gas, $N_2$, or a combination thereof, with an atmosphere consisting essentially of $N_2$ being most preferred. As noted above, use of such an atmosphere aids in minimizing oxidation of carbon-carbon double bonds of the polyunsaturated fatty acid esters.

After the precipitate comprising urea has formed, the precipitate preferably is separated from the liquid fraction enriched in polyunsaturated esters. This may be achieved, for example, by filtration or centrifugation. In a particularly preferred embodiment, the precipitate is subsequently washed with a small quantity of the organic solvent (preferably saturated with urea) to recover any residual unprecipitated desired polyunsaturated fatty acid ester that remains with the precipitate. This solvent, in turn, preferably is combined with the liquid fraction.

The liquid fraction preferably is concentrated, combined with water, and then the esters therein are preferably extracted with a non-polar solvent from the resulting mixture. The liquid fraction may be concentrated, for example, by evaporating a portion of the solvent from the liquid fraction (the amount of solvent evaporated, however, preferably is not so great as to cause further urea to precipitate). The amount of water subsequently combined with the resulting concentrated liquid fraction may vary widely. Preferably, the volume ratio of water to concentrated liquid fraction is about 2:1 (in a particularly preferred embodiment, sufficient acid (preferably HCl) is also introduced to neutralize the urea). The non-polar solvent that may be used to extract the fatty acid esters from the resulting concentrated-mother-liquor/water mixture may be, for example, petroleum ether, pentane, hexane, cyclohexane, ethyl acetate, or heptane, with hexane being the most preferred. The volumetric ratio of the non-polar solvent to the concentrated-mother-liquor/water mixture preferably is about 2:3.

In an especially preferred embodiment, the liquid fraction is also extracted with a slightly polar organic solvent to maximize recovery of the fatty acid esters (which, as noted above, are slightly polar). Examples of suitable slightly polar solvents include diethyl ether and ethyl acetate, with diethyl ether being most preferred. Preferably, the volumetric ratio of slightly polar solvent to the mother-liquor/water mixture is about 2:3. Following the extraction with this slightly polar solvent, the solvent preferably is combined with the non-polar solvent used in the initial extraction.

After the extraction is complete, any residual water may be removed from the extraction solvent by, for example, washing the solvent with brine and/or passing the solvent over an anhydrous salt (e.g., sodium sulfate). The solution then preferably is concentrated by, for example, evaporating a portion of the solvent.

2. Winterization

It has been found in accordance with this invention that winterization is a time-efficient alternative to urea crystallization for enriching the concentration of a polyunsaturated fatty acid ester in a fatty acid ester mixture comprising the polyunsaturated fatty acid ester and saturated fatty acid esters. Winterization comprises cooling a solution comprising the polyunsaturated fatty acid ester and the saturated fatty acid esters to a temperature which will cause at least a portion of the saturated fatty acid esters to precipitate, while causing a substantially less proportion of the desired polyunsaturated fatty acid ester to precipitate.

Winterization is typically conducted in an organic solvent that can solubilize the desired polyunsaturated fatty acid ester and at least one saturated fatty acid ester in the fatty acid ester mixture. Suitable solvents include, for example, methanol and ethanol, with methanol being the most preferred. Preferably, the volumetric ratio of the fatty acid ester mixture to the organic solvent is about 1:12.

Preferably, after the fatty acid mixture is dissolved in the organic solvent, the solution is cooled to a temperature which is low enough to cause a precipitate to form which comprises at least one saturated fatty acid ester. Preferably, however, the solution is not cooled to a temperature so low that the amount of the desired polyunsaturated fatty acid ester(s) (e.g., an ester of DHA and/or DPA) in the precipitate exceeds about 30 wt. % of the amount of desired polyunsaturated fatty acid ester(s) in the fatty acid mixture before conducting the winterization. More preferably, the solution is not cooled to a temperature so low that the amount of the desired polyunsaturated fatty acid ester(s) in the precipitate exceeds 25 wt. % of the amount of the desired polyunsaturated fatty acid ester(s) in the fatty acid mixture before conducting the winterization. And most preferably, the solution is not cooled to a temperature so low that the amount of the desired polyunsaturated fatty acid ester(s) in the precipitate exceeds 20 wt. % of the amount of the desired polyunsaturated fatty acid ester(s) in the fatty acid mixture before conducting the winterization. In a particularly preferred embodiment of this invention, the solution is cooled to a temperature which is no greater than about 0° C., more preferably from about −30 to about −10° C., still more preferably from about −25 to about −15° C., and most preferably about −20° C. The solution preferably is maintained at these temperatures for up to about 20 hours, and kept under a non-oxidizing atmosphere to minimize the oxidation of the carbon-carbon double bonds of the polyunsaturated fatty acid esters.

After forming the precipitate, the solution preferably is separated from the precipitate to form a liquid fraction enriched in the desired polyunsaturated fatty acid ester(s). This may be achieved, for example, by filtration or centrifugation. After the liquid fraction is separated, it may be concentrated by, for example, evaporating the solvent in a rotary evaporator.

DEFINITIONS

Unless otherwise stated, the following definitions should be used:

The term "hydrocarbyl" is defined as a radical consisting exclusively of carbon and hydrogen. The hydrocarbyl may be branched or unbranched, may be saturated or unsaturated, and may contain one or more rings. Suitable hydrocarbyl residues include alkyl, alkenyl, alkynyl, and aryl residues. They also include alkyl, alkenyl, alkynyl, and aryl residues substituted with other aliphatic or cyclic hydrocarbyl groups, such as alkaryl, alkenaryl and alkynaryl.

The term "substituted hydrocarbyl" is defined as a hydrocarbyl wherein at least one hydrogen atom has been substituted with an atom other than hydrogen. For example, the hydrogen atom may be replaced by a halogen atom, such as a chlorine or fluorine atom. The hydrogen atom alternatively may be substituted by an oxygen atom to form, for example, a hydroxy group, an ether, an ester, an anhydride, an aldehyde, a ketone, or a carboxylic acid. The hydrogen atom also may be replaced by a nitrogen atom to form, for example, an amide or a nitro functionality. To illustrate further, the hydrogen atom may be replaced with a sulfur atom to form, for example, $—SO_3H_2$.

With reference to the use of the word(s) "comprise" or "comprises" or "comprising" in this entire specification (including the claims below), Applicant notes that unless the context requires otherwise, those words are used on the basis and clear understanding that they are to be interpreted inclusively, rather than exclusively, and that Applicant intends each of those words to be so interpreted in construing this entire specification.

EXAMPLES

The following examples are simply intended to further illustrate and explain the present invention. This invention, therefore, should not be limited to any of the details in these examples.

Example 1

Base-Catalyzed Transesterification

Approximately 100 g of oil extracted from Schizochytrium sp. (SEAGOLD, Monsanto Co., St. Louis, Mo.) was dissolved in 100 ml of dichloromethane and 200 ml of methanol. Then 1 g of elemental sodium was added. The solution was refluxed for 10 min., and then poured into 500 ml of water containing 16 ml of 12N HCl. The aqueous layer was extracted 3 times with 400 ml of hexane. The 3 hexane layers were combined and washed with an aqueous solution containing 2% potassium bicarbonate, and finally dried over anhydrous sodium sulfate.

Example 2

Acid-Catalyzed Transesterification

A mixture of HCl and methanol was prepared by slowly adding 100 ml of acetylchloride to 1000 ml of methanol at 0° C. Approximately 30 g of oil extracted from Schizochytrium sp. was then added to 1000 ml of this mixture. The mixture was then stirred overnight under an $N_2$ atmosphere. Approximately 800 ml of ice cold (i.e., roughly 0° C.) distilled water was then added to the mixture, and the mixture was transferred to a separatory funnel where it was extracted three times with 200 ml of an organic solvent containing diethyl ether and petroleum ether. The volumetric ratio of the diethyl ether to petroleum ether in the solvent was approximately 1:9. The combined organic layer was then washed with brine (i.e., a saturated solution of NaCl) and dried over anhydrous sodium sulfate. The solvent in the organic layer was then evaporated using a rotary evaporator.

The yield of the transesterified product was 30 g. Gas chromatography of the product revealed that 9.5 wt. % consisted of the methyl ester of 14-carbon saturated fatty acid, 28.2 wt. % consisted of the methyl ester of 16-carbon saturated fatty acid, 14.3 wt. % consisted of the methyl ester of ω-6 DPA, and 36.2 wt. % consisted of the methyl ester of ω-3 DHA.

Example 3

Using Urea Crystallization to Increase Concentration of Methyl Ester of DHA

Approximately 50 g of methyl esters prepared using the technique of Example 2 were dissolved in 500 ml of methanol in a flask. Afterward, 100 g of urea was added, and the mixture was heated until essentially all the urea was dissolved. The flask was flushed with $N_2$ and sealed with aluminum foil, and then allowed to cool to room temperature (i.e., from about 20 to about 25° C.). The mixture was allowed to sit overnight with occasional swirling. The next day, the material was filtered through a Buchner funnel to remove the urea crystals. After washing the crystals twice with 25 ml of methanol (saturated with urea), the methanol was added to the filtrate. A portion of the methanol in the filtrate was then evaporated from the filtrate using a rotary evaporator until the filtrate had a volume of 150 ml. Approximately 300 ml of an aqueous solution of 1% HCl was then added to the filtrate. Afterward, this mixture was extracted with 300 ml of hexane and then with 300 ml of diethyl ether. The organic layers were combined and then washed twice with 50 ml of water, washed once with 50 ml of brine, and finally dried over anhydrous sodium sulfate. The solvent was then removed under reduced pressure.

Approximately 23 g of crude product was obtained. Gas chromatography of the product revealed that 23.4 wt. % consisted of the methyl ester of ω-6 DPA, 65.2 wt. % consisted of the methyl ester of ω-3 DHA, 2.9 wt. % consisted of the methyl ester of 14-carbon saturated fatty acid, and 1.5 wt. % consisted of the methyl ester of 16-carbon saturated fatty acid.

Example 4

Using Winterization to Increase Concentration of Methyl Ester of DHA

Approximately 15 g of methyl esters prepared using the technique of Example 2 were dissolved in 175 ml of methanol in a flask. The flask was flushed with $N_2$ and sealed with aluminum foil. The mixture was then placed into a −20° C. freezer overnight. The next day, the precipitate was filtered through a Buchner funnel.

Gas chromatography of the solid revealed that 14.4 wt. % consisted of 14-carbon saturated fatty acid, 60.6 wt. % consisted of 16-carbon fatty acid, 2.8 wt. % consisted of ω-6 DPA, and 17.0 wt. % consisted of ω-3 DHA The filtrate was concentrated to 9.3 g by evaporating a portion of the methanol in the filtrate using a rotary evaporator. Gas chromatography of this filtrate revealed that 20.8 wt. % consisted of ω-6 DPA, 57.9 wt. % consisted of ω-3 DHA, 9.0 wt. % consisted of 14-carbon saturated fatty acid, and 5.5 wt. % consisted of 16-carbon saturated fatty acid.

The above description of the preferred embodiment is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

I claim:

1. A process for making a mixture comprising a polyunsaturated fatty acid ester, said process comprising:

transesterifying an oil from Schizochytrium sp. with an alcohol in the presence of a base to form a saturated fatty acid ester and said polyunsaturated fatty acid ester, said fatty acid esters being formed from said alcohol and fatty acid residues of at least one glyceride in said oil;

dissolving urea in a medium comprising said fatty acid esters to form a medium comprising said fatty acid esters and dissolved urea;

cooling or concentrating said medium comprising said fatty acid esters and dissolved urea to form (a) a precipitate comprising urea and at least a portion of said saturated fatty acid ester, and (b) a liquid fraction comprising at least most of said polyunsaturated fatty acid ester; and separating said precipitate from said liquid fraction, wherein said polyunsaturated fatty acid ester has Formula (V):

(V)

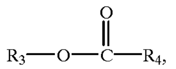

the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

2. A process according to claim 1, wherein $R_4$ comprises a straight chain hydrocarbyl comprising 21 carbon atoms and 5 carbon-carbon double bonds.

3. A process according to claim 1, wherein $R_4$ comprises a straight chain hydrocarbyl comprising 21 carbon atoms and 6 carbon-carbon double bonds.

4. A process according to claim 1, wherein said glyceride (s) comprises a triglyceride.

5. A process according to claim 1, wherein $R_3$ comprises a hydrocarbyl comprising from 1 to 4 carbon atoms.

6. A process according to claim 5, wherein $R_3$ comprises methyl.

7. A process according to claim 5, wherein $R_3$ comprises ethyl.

8. A process according to claim 1, wherein said base comprises NaOH or KOH.

9. A process according to claim 1, wherein said base comprises elemental sodium.

10. A process according to claim 1, wherein said transesterification comprises hydrolysis of said glyceride(s) to form free fatty acids, followed by esterification of said free fatty acids.

11. A process according to claim 1, wherein said glyceride (s) is contacted with said alcohol in the presence of said base in a liquid that further comprises an organic solvent that can solubilize said glyceride(s).

12. A process according to claim 11, wherein said organic solvent comprises dichloromethane.

13. A process according to claim 11, wherein said glyceride(s) is contacted with said alcohol in the presence of said base at a temperature which is greater than the boiling point of said organic solvent.

14. A process according to claim 1, wherein said glyceride (s) is contacted with said alcohol in the presence of said base at a temperature of at least about 40° C.

15. A process according to claim 14, wherein said temperature is from about 70 to about 150° C.

16. A process according to claim 1, wherein said glyceride (s) is contacted with said alcohol in the presence of said base to form a mixture which is then heated under reflux to form said fatty acid esters.

17. A process according to claim 1, wherein said fatty acid esters are formed under a non-oxidizing atmosphere.

18. A process according to claim 1, wherein said medium comprising said fatty acid esters and dissolved urea further comprises an organic solvent that can solubilize said polyunsaturated fatty acid ester.

19. A process according to claim 18, wherein said organic solvent comprises an alkyl alcohol comprising from 1 to 4 carbon atoms.

20. A process according to claim 19, wherein said organic solvent comprises ethanol.

21. A process according to claim 1, wherein said medium comprising said fatty acid esters and dissolved urea is cooled to a temperature of no less than about 15° C. to form said urea-containing precipitate.

22. A process according to claim 21, wherein said temperature is no less than about 20° C.

23. A process according to claim 21, wherein said temperature is from about 15 to about 25° C.

24. A process according to claim 21, wherein said temperature is from about 20 to about 25° C.

25. A process according to claim 1, wherein at least a portion of said precipitate is formed under a non-oxidizing atmosphere.

26. A process according to claim 1, wherein said saturated fatty acid ester has Formula (VI):

(VI)

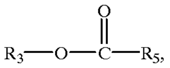

wherein $R_5$ is a hydrocarbyl comprising no double bonds.

27. A process according to claim 26, wherein $R_5$ comprises 13 or 15 carbon atoms.

28. A process for making a mixture comprising a polyunsaturated fatty acid ester, said process comprising:

transesterifying an oil from Schizochytrium sp. with an alcohol in the presence of an acid to form a saturated fatty acid ester and said polyunsaturated fatty acid ester, said fatty acid esters being formed from said alcohol and fatty acid residues of at least one glyceride in said oil;

dissolving urea in a medium comprising said fatty acid esters to form a medium comprising said fatty acid esters and dissolved urea;

cooling said medium comprising said fatty acid esters and dissolved urea to a temperature of no less than about 15° C. to form (a) a precipitate comprising urea and at least a portion of said saturated fatty acid ester, and (b) a liquid fraction comprising at least most of said polyunsaturated fatty acid ester; and separating said precipitate from said liquid fraction, wherein said polyunsaturated fatty acid ester has Formula (V):

(V)

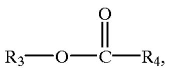

the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

29. A process according to claim 28, wherein said acid comprises HCl.

30. A process according to claim 28, wherein $R_4$ comprises a straight chain hydrocarbyl comprising 21 carbon atoms and 6 carbon-carbon double bonds.

31. A process according to claim 28, wherein $R_3$ comprises ethyl.

32. A process according to claim 28, wherein said polyunsaturated fatty acid esters are formed under a non-oxidizing atmosphere.

33. A process according to claim 28, wherein said medium comprising said fatty acid esters and dissolved urea further comprises an organic solvent that can solubilize said polyunsaturated fatty acid ester.

34. A process according to claim 33, wherein said organic solvent comprises ethanol.

35. A process according to claim 33, wherein said medium comprising said fatty acid esters and dissolved urea is cooled to a temperature of no less than about 20° C. to form said precipitate.

36. A process according to claim 33, wherein said medium comprising said fatty acid esters and dissolved urea is cooled to a temperature of from about 15 to about 25° C. to form said precipitate.

37. A process according to claim 33, wherein said medium comprising said fatty acid esters and dissolved urea is cooled to a temperature of from about 20 to about 25° C. to form said precipitate.

38. A process according to claim 28, wherein at least a portion of said precipitate is formed under a non-oxidizing atmosphere.

39. A process according to claim 28, wherein the saturated fatty acid ester has Formula (VI):

(VI)

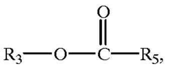

wherein $R_5$ is a hydrocarbyl comprising no double bonds.

40. A process according to claim 39, wherein $R_5$ comprises 13 or 15 carbon atoms.

41. A process for making a mixture comprising a polyunsaturated fatty acid ester, the process comprising:

transesterifying an oil from Schizochytrium sp. with an alcohol in the presence of an acid to form a reaction mixture comprising a saturated fatty acid ester and said polyunsaturated fatty acid ester, said fatty acid esters being formed from said alcohol and fatty acid residues of at least one glyceride in said oil;

separating at least most of said polyunsaturated fatty acid ester from said reaction mixture to form a mixture comprising said polyunsaturated fatty acid and a residual amount of said saturated fatty acid ester;

dissolving urea in a medium comprising said separated polyunsaturated fatty acid ester and residual saturated fatty acid ester to form a medium comprising said separated polyunsaturated fatty acid ester, residual saturated fatty acid ester, and dissolved urea;

cooling or concentrating said medium comprising said separated polyunsaturated fatty acid ester, residual saturated fatty acid ester, and dissolved urea to form (a) a precipitate comprising urea and at least a portion of said residual saturated fatty acid ester, and (b) a liquid fraction comprising at least most of said separated polyunsaturated fatty acid ester; and separating said precipitate from said liquid fraction, wherein said polyunsaturated fatty acid ester has Formula (V):

(V)

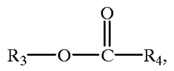

the alcohol is $R_3$—OH, $R_3$ is a hydrocarbyl or a substituted hydrocarbyl, and $R_4$ is a straight chain hydrocarbyl comprising 21 carbon atoms and at least 2 carbon-carbon double bonds.

42. A process according to claim 41, wherein $R_4$ comprises a straight chain hydrocarbyl comprising 21 carbon atoms and 6 carbon-carbon double bonds.

43. A process according to claim 41, wherein $R_3$ comprises ethyl.

44. A process according to claim 41, wherein said separation of said polyunsaturated fatty acid ester from at least a portion of said reaction mixture comprises extracting said polyunsaturated fatty acid ester from said reaction mixture using a non-polar organic solvent.

45. A process according to claim 44, wherein said non-polar solvent comprises petroleum ether, pentane, hexane, cyclohexane, or heptane.

46. A process according to claim 44, wherein said non-polar solvent comprises hexane.

47. A process according to claim 41, wherein said separation of said polyunsaturated fatty acid ester from at least a portion of said reaction mixture comprises extracting said polyunsaturated fatty acid ester from said reaction mixture using a non-polar solvent and a polar organic solvent.

48. A process according to claim 47, wherein said polar solvent comprises diethyl ether.

49. A process for making a mixture comprising a polyunsaturated fatty acid ester, said process comprising:

transesterifying an oil from Schizochytrium sp. with an alcohol in the presence of an acid to form a saturated fatty acid ester and said polyunsaturated fatty acid ester, said fatty acid esters being formed from said alcohol and fatty acid residues of at least one glyceride in said oil;

dissolving urea in a median comprising said fatty acid esters to form a medium comprising said fatty acid esters and dissolved urea;

cooling said medium comprising said fatty acid esters and dissolved urea to a temperature of no less than 10° C. to form (a) a precipitate comprising urea and at least a portion of said saturated fatty acid ester, and (b) a liquid fraction comprising at least most of said polyunsaturated fatty acid ester; and separating said precipitate from said liquid fraction, wherein said polyunsaturated fatty acid ester has Formula (V):

(V)

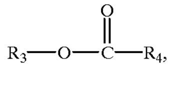

the alcohol is $R_3$—OH, $R_3$ comprises at least 2 carbon atoms and is a hydrocarbyl or substituted hydrocarbyl, and $R_4$ is a straight chain hydrocarbyl comprising 21 carbon atoms and at least 2 carbon-carbon double bonds.

50. A process according to claim 49, wherein $R_3$ comprises ethyl.

51. A process according to claim 49, wherein said medium comprising said fatty acid esters and dissolved urea is cooled to a temperature of no less than about 15° C. to form said precipitate.

52. A process according to claim 51, wherein said temperature is no less than about 20° C.

53. A process according to claim 51, wherein said temperature is from about 20 to about 25° C.

54. A process according to claim 49, wherein said fatty acid esters are formed under a non-oxidizing atmosphere.

55. A process according to claim 49, wherein at least a portion of said precipitate is formed under a non-oxidizing atmosphere.

56. A process for making a mixture comprising a polyunsaturated fatty acid ester, said process comprising:

forming said polyunsaturated fatty acid ester and a saturated fatty acid ester, said fatty acid esters being derived from at least one glyceride obtained from Schizochytrium sp.;

cooling a solvent comprising said fatty acid esters to a temperature of no less than about −30° C. and no greater than about 0° C. to form (a) a precipitate comprising at least a portion of said saturated fatty acid ester, and (b) a liquid fraction comprising at least most of said polyunsaturated fatty acid ester;

separating said precipitate from said liquid fraction, wherein said polyunsaturated fatty acid ester has Formula (V):

(V)

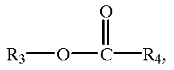

the saturated fatty acid ester has Formula (VI):

(VI)

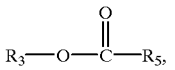

$R_3$ is a hydrocarbyl or a substituted hydrocarbyl, $R_4$ is a straight chain hydrocarbyl comprising 21 carbon atoms and at least 2 carbon-carbon double bonds, and $R_5$ is a hydrocarbyl comprising no double bonds.

57. A process according to claim 56, wherein $R_3$ comprises ethyl.

58. A process according to claim 56, wherein said solvent comprising said fatty acid esters comprises an organic solvent that can solubilize said polyunsaturated fatty acid ester.

59. A process according to claim 58, wherein said organic solvent comprises methanol.

60. A process according to claim 56, wherein at least a portion of said precipitate is formed under a non-oxidizing atmosphere.

61. A process according to claim 56, wherein said temperature is no greater than about −10° C.

62. A process according to claim 56, wherein said temperature is no greater than about −20° C.

63. A process according to claim 56, wherein said fatty acid esters are formed by a process comprising contacting an oil from Schizochytrium sp. with an alcohol in the presence of a base or acid, wherein said fatty acid esters are formed from said alcohol and fatty acid residues of at least one glyceride in said oil, and said alcohol is $R_3$—OH.

64. A process according to claim 63, wherein said fatty acid esters are formed under a non-oxidizing atmosphere.

* * * * *